United States Patent
Rockweiler et al.

(10) Patent No.: US 11,471,688 B2
(45) Date of Patent: *Oct. 18, 2022

(54) AMBULATORY PHRENIC NERVE STIMULATION DETECTION

(71) Applicant: Cardiac Pacemakers, Inc., St. Paul, MN (US)

(72) Inventors: Holly E. Rockweiler, San Francisco, CA (US); Sunipa Saha, Shoreview, MN (US); Aaron R. McCabe, Edina, MN (US); Krzysztof Z. Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 132 days.

This patent is subject to a terminal disclaimer.

(21) Appl. No.: 16/157,971

(22) Filed: Oct. 11, 2018

(65) Prior Publication Data

US 2019/0060652 A1 Feb. 28, 2019

Related U.S. Application Data

(63) Continuation of application No. 15/237,831, filed on Aug. 16, 2016, now Pat. No. 10,124,174, which is a (Continued)

(51) Int. Cl.
*A61N 1/37* (2006.01)
*A61N 1/365* (2006.01)
*A61N 1/362* (2006.01)

(52) U.S. Cl.
CPC ......... *A61N 1/3702* (2013.01); *A61N 1/3627* (2013.01); *A61N 1/36542* (2013.01)

(58) Field of Classification Search
CPC ............ A61N 1/36128; A61N 1/36132; A61N 1/36135; A61N 1/36142

See application file for complete search history.

(56) References Cited

U.S. PATENT DOCUMENTS

| 4,907,593 | A | 3/1990 | Rapach et al. |
| 6,277,072 | B1 | 8/2001 | Bardy |

(Continued)

FOREIGN PATENT DOCUMENTS

| CN | 2756256 Y | 2/2006 |
| CN | 104321107 A | 1/2015 |

(Continued)

OTHER PUBLICATIONS

"U.S. Appl. No. 13/781,042, Non Final Office Action dated May 15, 2014", 14 pgs.

(Continued)

*Primary Examiner* — Allen Porter
(74) *Attorney, Agent, or Firm* — Schwegman Lundberg & Woessner, P.A.

(57) ABSTRACT

An example of a system includes an implantable medical device (IMD) for implantation in a patient, where the IMD includes a cardiac pace generator, phrenic nerve stimulation (PS) sensor, a memory, and a controller, and where the controller is operably connected to the cardiac pace generator to generate cardiac paces. The controller is configured to provide a trigger for conducting a PS detection procedure and perform the PS detection procedure in response to the trigger. In performing the PS detection procedure the controller is configured to receive a signal from the sensor, detect PS using the signal from the sensor, and record the PS detection in storage within the IMD.

20 Claims, 8 Drawing Sheets

Related U.S. Application Data continuation of application No. 14/191,193, filed on Feb. 26, 2014, now Pat. No. 9,421,383.

(60) Provisional application No. 61/779,772, filed on Mar. 13, 2013.

(56) References Cited

U.S. PATENT DOCUMENTS

| | | |
|---|---|---|
| 7,142,919 B2 | 11/2006 | Hine et al. |
| 7,299,093 B2 | 11/2007 | Zhu et al. |
| 7,354,404 B2 | 4/2008 | Kim et al. |
| 7,426,412 B1 | 9/2008 | Schecter |
| 7,477,932 B2 | 1/2009 | Lee et al. |
| 7,499,751 B2 | 3/2009 | Meyer et al. |
| 7,636,599 B1 | 12/2009 | Koh et al. |
| 7,890,159 B2 | 2/2011 | Zhang et al. |
| 7,972,276 B1 | 7/2011 | Min |
| 8,326,418 B2 | 12/2012 | Sommer et al. |
| 8,326,420 B2 | 12/2012 | Skelton et al. |
| 8,527,051 B1 * | 9/2013 | Hedberg ............ A61N 1/36521 607/18 |
| 8,532,774 B1 | 9/2013 | Hedberg et al. |
| 8,626,292 B2 | 1/2014 | Mccabe et al. |
| 8,634,915 B2 | 1/2014 | Mccabe et al. |
| 8,958,876 B2 | 2/2015 | Dong et al. |
| 9,031,651 B2 | 5/2015 | Rockweiler et al. |
| 9,211,415 B2 | 12/2015 | Saha et al. |
| 9,272,151 B2 | 3/2016 | Siejko et al. |
| 9,421,383 B2 | 8/2016 | Rockweiler et al. |
| 10,124,174 B2 | 11/2018 | Rockweiler et al. |
| 10,413,203 B2 | 9/2019 | Saha et al. |
| 2003/0065365 A1 | 4/2003 | Zhu et al. |
| 2005/0145246 A1 | 7/2005 | Hartley et al. |
| 2005/0240240 A1 * | 10/2005 | Park ..................... A61N 1/3601 607/42 |
| 2007/0213778 A1 | 9/2007 | Burnes et al. |
| 2008/0288023 A1 | 11/2008 | John |
| 2009/0043351 A1 | 2/2009 | Sathaye et al. |
| 2009/0210024 A1 | 8/2009 | Brooke |
| 2010/0010590 A1 | 1/2010 | Skelton et al. |
| 2010/0262204 A1 | 10/2010 | Mccabe et al. |
| 2010/0305637 A1 | 12/2010 | McCabe et al. |
| 2010/0305638 A1 * | 12/2010 | McCabe ............ A61N 1/3706 607/11 |
| 2010/0305647 A1 | 12/2010 | Mccabe et al. |
| 2011/0004264 A1 | 1/2011 | Siejko et al. |
| 2011/0054559 A1 | 3/2011 | Rosenberg et al. |
| 2011/0152956 A1 * | 6/2011 | Hincapie Ordonez ...................... A61B 5/4041 607/4 |
| 2012/0035685 A1 | 2/2012 | Saha et al. |
| 2012/0078320 A1 | 3/2012 | Schotzko et al. |
| 2012/0296388 A1 | 11/2012 | Zhang et al. |
| 2013/0060298 A1 | 3/2013 | Splett et al. |
| 2013/0261471 A1 | 10/2013 | Saha et al. |
| 2013/0261476 A1 | 10/2013 | Rockweiler et al. |
| 2013/0261688 A1 | 10/2013 | Dong et al. |
| 2013/0289640 A1 | 10/2013 | Zhang et al. |
| 2013/0310891 A1 * | 11/2013 | Enrooth ............... A61N 1/3686 607/30 |
| 2014/0005742 A1 * | 1/2014 | Mahajan ............ A61N 1/36514 607/28 |
| 2014/0018872 A1 | 1/2014 | Siejko et al. |
| 2014/0018875 A1 | 1/2014 | Brisben et al. |
| 2014/0088661 A1 | 3/2014 | Hincapie Ordonez et al. |
| 2014/0100626 A1 | 4/2014 | Mccabe et al. |
| 2014/0128933 A1 | 5/2014 | Brooke |
| 2014/0277244 A1 | 9/2014 | Rockweiler et al. |
| 2014/0277280 A1 | 9/2014 | Saha et al. |
| 2016/0035461 A1 | 12/2016 | Rockweiler et al. |
| 2019/0365261 A1 | 12/2019 | Saha et al. |

FOREIGN PATENT DOCUMENTS

| | | |
|---|---|---|
| CN | 104321107 B | 10/2016 |
| JP | 2011510713 A | 4/2011 |
| JP | 2015515307 A | 5/2015 |
| WO | WO-2009102726 A1 | 8/2009 |
| WO | WO-2010138739 A1 | 12/2010 |
| WO | WO-2011084325 A1 | 7/2011 |
| WO | WO-2013148053 A1 | 10/2013 |

OTHER PUBLICATIONS

"U.S. Appl. No. 13/781,042, Notice of Allowance dated Oct. 15, 2014", 7 pgs.

"U.S. Appl. No. 13/781,042, Response filed Aug. 12, 2014 to Non Final Office Action dated 05-15-24", 14 pgs.

"U.S. Appl. No. 13/781,133, Advisory Action dated Sep. 27, 2016", 5 pgs.

"U.S. Appl. No. 13/781,133, Final Office Action dated Apr. 14, 2016", 26 pgs.

"U.S. Appl. No. 13/781,133, Non Final Office Action dated Aug. 14, 2015", 20 pgs.

"U.S. Appl. No. 13/781,133, Non Final Office Action dated Dec. 15, 2016", 22 pgs.

"U.S. Appl. No. 13/781,133, Response filed Apr. 17, 2017 to Non Final Office Action dated Dec. 15, 2016", 14 pgs.

"U.S. Appl. No. 13/781,133, Response filed Jul. 13, 2016 to Final Office Action dated Apr. 14, 2016", 13 pgs.

"U.S. Appl. No. 13/781,133, Response filed Oct. 12, 2016 to FinalOffice Action dated Apr. 14, 2016", 15 pgs.

"U.S. Appl. No. 13/781,133, Response filed Nov. 17, 2015 to Non Final Office Action dated Aug. 14, 2015", 18 pgs.

"U.S. Appl. No. 13/781,177, Non Final Office Action dated Apr. 17, 2014", 14 pgs.

"U.S. Appl. No. 13/781,177, Notice of Allowance dated Jan. 14, 2015", 7 pgs.

"U.S. Appl. No. 13/781,177, Notice of Allowance dated Sep. 18, 2014", 7 pgs.

"U.S. Appl. No. 13/781,177, Response filed Aug. 18, 2014 to Non Final Office Action dated Apr. 17, 2014", 12 pgs.

"U.S. Appl. No. 13/939,790, Examiner Interview Summary dated Oct. 19, 2015", 3 pgs.

"U.S. Appl. No. 13/939,790, Final Office Action dated Aug. 17, 2015", 8 pgs.

"U.S. Appl. No. 13/939,790, Non Final Office Action dated Apr. 1, 2015", 7 pgs.

"U.S. Appl. No. 13/939,790, Notice of Allowance dated Oct. 22, 2015", 7 pgs.

"U.S. Appl. No. 13/939,790, Response filed Jun. 30, 2015 to Non Final Office Action dated Apr. 1, 2015", 9 pgs.

"U.S. Appl. No. 13/939,790, Response filed Oct. 15, 2015 to Final Office Action dated Aug. 17, 2015", 10 pgs.

"U.S. Appl. No. 14/191,094, Non Final Office Action dated Apr. 3, 2015", 8 pgs.

"U.S. Appl. No. 14/191,094, Notice of Allowance dated Aug. 12, 2015", 7 pgs.

"U.S. Appl. No. 14/191,094, Response filed Jul. 3, 2015 to Non Final Office Action dated Apr. 3, 2015", 12pgs-.

"U.S. Appl. No. 14/191,193, Advisory Action dated Jun. 8, 2015", 6 pgs.

"U.S. Appl. No. 14/191,193, Final Office Action dated Feb. 16, 2016", 16 pgs.

"U.S. Appl. No. 14/191,193, Final Office Action dated Mar. 30, 2015", 12 pgs.

"U.S. Appl. No. 14/191,193, Non Final Office Action dated Oct. 2, 2015", 13 pgs.

"U.S. Appl. No. 14/191,193, Non Final Office Action dated Oct. 28, 2014", 15 pgs.

"U.S. Appl. No. 14/191,193, Notice of Allowance dated Apr. 25, 2016", 13 pgs.

"U.S. Appl. No. 14/191,193, Respnse filed Apr. 8, 2016 to Final Office Action dated Feb. 16, 2016", 12 pgs.

(56) References Cited

OTHER PUBLICATIONS

"U.S. Appl. No. 14/191,193, Response filed Jan. 4, 2016 to Non Final Office Action dated Oct. 2, 2015", 9 pgs.
"U.S. Appl. No. 14/191,193, Response filed Jan. 26, 2015 to Non Final Office Action dated Oct. 28, 2014", 12 pgs.
"U.S. Appl. No. 14/191,193, Response filed May 28, 2015 to Final Office Action dated Mar. 30, 2015", 11 pgs.
"U.S. Appl. No. 14/191,193, Response filed Jun. 30, 2015 to Final Office Action dated Mar. 30, 2015", 9 pgs.
"U.S. Appl. No. 15/237,831, Advisory Action dated Aug. 15, 2017", 4 pgs.
"U.S. Appl. No. 15/237,831, Examiner Interview Summary dated Jun. 6, 2018", 2 pgs.
"U.S. Appl. No. 15/237,831, Examiner Interview Summary dated Jul. 26, 2017", 2 pgs.
"U.S. Appl. No. 15/237,831, Final Office Action dated Mar. 27, 2018", 13 pgs.
"U.S. Appl. No. 15/237,831, Final Office Action dated May 23, 2017", 10 pgs.
"U.S. Appl. No. 15/237,831, Non Final Office Action dated Sep. 26, 2017", 10 pgs.
"U.S. Appl. No. 15/237,831, Non Final Office Action dated Nov. 28, 2016", 10 pgs.
"U.S. Appl. No. 15/237,831, Notice of Allowance dated Jul. 10, 2018", 8 pgs.
"U.S. Appl. No. 15/237,831, Preliminary Amendment filed Aug. 29, 2016", 7 pgs.
"U.S. Appl. No. 15/237,831, Response filed Mar. 27, 2017 to Non Final Office Action dated Nov. 28, 2016", 8 pgs.
"U.S. Appl. No. 15/237,831, Response filed Jun. 4, 2018 to Final Office Action dated Mar. 27, 2018", 9 pgs.
"U.S. Appl. No. 15/237,831, Response filed Jul. 24, 2017 to Final Office Action dated—May 23, 2017", 9 pgs.
"U.S. Appl. No. 15/237,831, Response filed Aug. 15, 2017 to Advisory Action dated Aug. 15, 2017", 11 pgs.
"U.S. Appl. No. 15/237,831, Response filed Dec. 22, 2017 to Non Final Office Action dated Sep. 26, 2017", 10 pgs.
"Chinese Application Serial No. 201380026426.8, Office Action dated Jun. 30, 2015", 13 pgs.
"International Application Serial No. PCT/US2013/028315, International Preliminary Report on Patentability dated Oct. 9, 2014", 8 pgs.
"International Application Serial No. PCT/US2013/028315, International Search Report dated Jul. 11, 2013", 3 pgs.
"International Application Serial No. PCT/US2013/028315, Written Opinion dated Jul. 11, 2013", 6 pgs.
"Japanese Application Serial No. 2015-503218, Notification of Reasons for Rejection dated Oct. 27, 2015", 2 pgs.
U.S. Appl. No. 13/781,133, filed Feb. 28, 2013, Baseline Determination for Phrenic Nerve Stimulation Detection.
U.S. Appl. No. 13/781,042, filed Feb. 28, 2013, Determination of Phrenic Nerve Stimulation Threshold, U.S. Pat. No. 8,958,876.
U.S. Appl. No. 13/781,177, filed Feb. 28, 2013, Phrenic Nerve Stimulation Detection, U.S. Pat. No. 9,031,651.
U.S. Appl. No. 13/939,790, filed Jul. 11, 2013, Adaptive Phrenic Nerve Stimulation Detection, U.S. Pat. No. 9,272,151.
U.S. Appl. No. 14/191,094, filed Feb. 26, 2014, Phrenic Nerve Stimulation Detection With Posture Sensing, U.S. Pat. No. 9,211,415.
U.S. Appl. No. 14/191,193, filed Feb. 26, 2014, Ambulatory Phrenic Nerve Stimulation Detection, U.S. Pat. No. 9,421,383.
U.S. Appl. No. 15/237,831, filed Aug. 16, 2016, Ambulatory Phrenic Nerve Stimulation Detection.
"U.S. Appl. No. 13/781,133, Advisory Action dated Sep. 28, 2018", 4 pgs.
"U.S. Appl. No. 13/781,133, Appeal Brief filed Jan. 22, 2019", 28 pgs.
"U.S. Appl. No. 13/781,133, Final Office Action dated Jun. 21, 2018", 23 pgs.
"U.S. Appl. No. 13/781,133, Non Final Office Action dated Oct. 2, 2017", 20 pgs.
"U.S. Appl. No. 13/781,133, Notice of Allowance dated May 6, 2019", 8 pgs.
"U.S. Appl. No. 13/781,133, Response filed Jan. 2, 2018 to Non Final Office Action dated Oct. 2, 2017", 12 pgs.
"U.S. Appl. No. 13/781,133, Response filed Aug. 21, 2018 to Final Office Action dated Jun. 21, 2018", 16 pgs.
"U.S. Appl. No. 16/539,905, Preliminary Amendment filed Aug. 15, 2019", 8 pgs.
"Chinese Application Serial No. 201380026426.8, Office Action dated Mar. 24, 2016", (W/English Translation), 8 pgs.
Dong, Yanting, et al., "Determination of Phrenic Nerve Stimulation Threshold", U.S. Appl. No. 13/781,042, filed Feb. 28, 2013, 69 pgs.
Mahajan, Deepa, et al., "System and Method for Selection of Pacing Vectors", U.S. Appl. No. 13/925,427, filed Jun. 24, 2013, 45 pgs.
Rockweiler, Holly, et al., "Phrenic Nerve Stimulation Detection", U.S. Appl. No. 13/781,177, filed Feb. 28, 2013, 69 pgs.

* cited by examiner

AMBULATORY PHRENIC NERVE STIMULATION DETECTION

CLAIM OF PRIORITY

This application is a continuation of U.S. application Ser. No. 15/237,831, filed Aug. 16, 2016, which is a continuation of U.S. application Ser. No. 14/191,193, filed Feb. 26, 2014, now issued as U.S. Pat. No. 9,421,383, which claims the benefit of priority under 35 U.S.C. § 119(e) of U.S. Provisional Patent Application Ser. No. 61/779,772, filed on Mar. 13, 2013, each of which is herein incorporated by reference in its entirety.

TECHNICAL FIELD

This application is related generally to medical devices and, more particularly, to systems, devices and methods that detect pace-induced phrenic nerve stimulation.

BACKGROUND

Implanted pacing systems may be used to pace the heart. When the heart is paced in the left ventricle (LV), for example, there may be unwanted stimulation of the phrenic nerve that causes contraction of the diaphragm. Unintended phrenic nerve activation (an unintended action potential propagated in the phrenic nerve that causes a noticeable diaphragm contraction) is a well-known consequence of left ventricular pacing. The left phrenic nerve, for example, descends on the pericardium to penetrate the left part of the diaphragm. In most people, the left phrenic nerve runs close to the coronary vein targets for LV lead placement. The unintended phrenic nerve activation may cause the diaphragm to undesirably contract. Unintended phrenic nerve activation may feel like hiccups to the patient. Such unintended phrenic nerve activation can occur when the electric field of the LV pacing lead is proximate to the left phrenic nerve and is at a stimulation output that is strong enough to capture the nerve. Unintended phrenic nerve activation may vary from patient to patient. One reason for this variance is that the anatomic location of the phrenic nerve can vary within patients. Additionally, the veins in which the cardiac lead may be placed are not always in the same location with respect to the ventricle and the nearby passing nerve. Also, the selected position in which to place a cardiac lead for a prescribed cardiac therapy may vary.

Although phrenic nerve stimulation is commonly assessed at implant, unintended phrenic nerve activation caused by phrenic nerve capture during pacing may first appear or worsen post-implant for a variety of reasons. Therefore, special office visits after implant may be necessary or desirable to reprogram the device or worse, surgically reposition the lead to avoid phrenic nerve stimulation.

SUMMARY

An example of a system includes an implantable medical device (IMD) for implantation in a patient. The IMD may include a cardiac pace generator, a phrenic nerve stimulation (PS) sensor, a memory, and a controller. The controller may be operably connected to the cardiac pace generator to generate cardiac paces. The controller may be configured to provide a trigger for conducting a PS detection procedure and perform the PS detection procedure in response to the trigger. In performing the PS detection procedure the controller may be configured to receive a signal from the PS sensor, detect PS using the signal from the PS sensor, and record the PS detection in storage within the IMD.

An example of a system comprises an implantable medical device (IMD) for implantation in a patient. The IMD may include a cardiac pace generator, phrenic nerve stimulation (PS) sensor, a memory, and a controller. The controller may be operably connected to the cardiac pace generator to generate cardiac paces, and the controller may include a trigger module, a recognition module, a PS test module and a decision module. The trigger module may be configured to provide a trigger for a PS detection procedure and to perform the base test. In performing the base test the trigger module may be configured to: detect an amplitude of the signal from the PS sensor, compare the sensed amplitude to a threshold to detect PS, and provide the trigger from the trigger module when the sensed amplitude is higher than the threshold. The recognition module may be configured to analyze a signal from the PS sensor to confirm the PS detection from the base test. The PS test module may be configured to respond to the PS detection confirmed by the recognition module. In responding to the PS detection confirmed by the recognition module, the PS test module is configured to further analyze the signal from the PS sensor to provide further confirmation of the PS detection. Confirmation by the PS test module may provide greater confidence than confirmation by the recognition module. The decision module may be configured to record the PS detection in the storage within the IMD, automatically change a current pacing configuration to another pacing configuration based at least in part on PS detection, or communicate an alert to an external device based at least in part on PS detection.

An example of a method is performed using an implantable medical device (IMD) within an ambulatory patient, where the IMD includes an accelerometer sensor for phrenic nerve stimulation (PS) detection. The method may comprise triggering a PS detection procedure using the IMD within an ambulatory patient, and performing the PS procedure in response to the trigger, wherein performing the PS procedure includes providing a signal from the PS detector, detecting PS using the signal from the PS detector, and recording the PS detection in storage within the IMD.

This Summary is an overview of some of the teachings of the present application and is not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 8A illustrates no PS in the streaming signal and FIG. 8B illustrates occurrences of PS in the streaming signal.

DETAILED DESCRIPTION

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter.

References to "an," "one," or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Some embodiments, for example, implement an automatic detection algorithm for detecting unintended phrenic nerve activation (also referred to herein as pace-induced phrenic nerve stimulation or as phrenic nerve stimulation "PS"). According to various embodiments, the PS detection procedure can be used in a clinical setting such as during implant procedures or in patient follow-up visits, or in an ambulatory setting such as in a patient's home, or in both the clinical and ambulatory setting. The PS detection procedure can lessen or alleviate the burden of the patients and clinical staff to adequately address the problems of unintended PS that can occur during myocardial stimulation. For example, the ability to accurately and/or automatically detect PS can reduce prolonged discomfort for patients experiencing PS, and can reduce the burden on hospitals and staff for testing and reprogramming devices.

As PS may be an unintended side effect of some cardiac pacing therapies, a brief discussion of myocardial stimulation and the phrenic nerve is provided below.

Myocardial Stimulation and the Phrenic Nerve

A myocardial stimulation therapy may deliver a cardiac therapy using electrical stimulation of the myocardium. Some examples of myocardial stimulation therapies, and devices for performing the therapies, are provided below. A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and then to the ventricular myocardium to provide a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure. Heart failure refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. A CRT example applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-myocardial infarction (MI) and heart failure patients, which appears to occur as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions may be the trigger for ventricular remodeling. Pacing one or more sites may cause a more coordinated contraction, by providing pre-excitation of myocardial regions which would otherwise be activated later during systole and experience increased wall stress. The pre-excitation of the remodeled region relative to other regions unloads the region from mechanical stress and allows reversal or prevention of remodeling to occur.

Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected. ATP may be referred to as overdrive pacing. Other overdrive pacing therapies exist, such as intermittent pacing therapy (IPT), which may also be referred to as a conditioning therapy.

Both a right phrenic nerve and a left phrenic nerve pass near the heart and innervate the diaphragm below the heart. Pace-induced phrenic nerve stimulation, also referred to herein as PS, may be observed with various forms of pacing. PS may be observed particularly with LV pacing because of the close proximity of the LV pacing site to the left phrenic nerve. PS is a common side effect of CRT. Cardiac stimulation at other locations of the heart may result in PS in either the left or right phrenic nerve. The present subject matter is not limited to PS of the left phrenic nerve during LV pacing, but may be implemented to appropriately address PS in either the left or right phrenic nerve caused by myocardial stimulation or other stimulation.

During a cardiac lead implant procedure such as an LV lead implant, for example, a physician may test for the presence of phrenic nerve stimulations (PS) for different pacing configurations and different stimulation parameters. Examples of pacing configurations can include, but are not limited to, LV bipolar, LV to can, and LV to right ventricle (RV) and examples of stimulation parameters can include an amplitude (e.g. voltage) and pulse width of stimulation pulses. Accordingly, the physician can program the IMD to deliver the cardiac therapy using only those pacing configurations or the stimulation parameters of the cardiac therapy that inhibits the unintended PS.

The PS procedure is capable of addressing problems with automatically detecting PS. Even when a patient is sitting quietly, it can be difficult to sense signals close to the PS threshold as the signal can be small. A PS threshold represents a smallest pacing parameter, such as a pacing amplitude for an LV pace, at which it can be determined that PS occurs with the pace. Thus, for example, PS is determined to generally occur when the pacing amplitude is equal to or greater than the PS threshold. PS may not occur for every pace equal to or greater than the PS threshold.

For example, it can be difficult to process low-peak-to-peak amplitudes of sensed PS responses from the deflection variations observed in the accelerometer or other PS sensor, especially those close to the PS threshold. It can also be difficult to detect PS because different patients have PS responses of various amplitudes and morphologies.

PS may be observed only when a patient is in a particular position (e.g. lying down) or when participating in certain activities or activity levels. The PS may not have been observed at the time that the stimulation device was implanted because of the patient position at the time of implantation, because of the effects of anesthesia, or because of other factors that are not present in a clinical setting.

Figure 1:
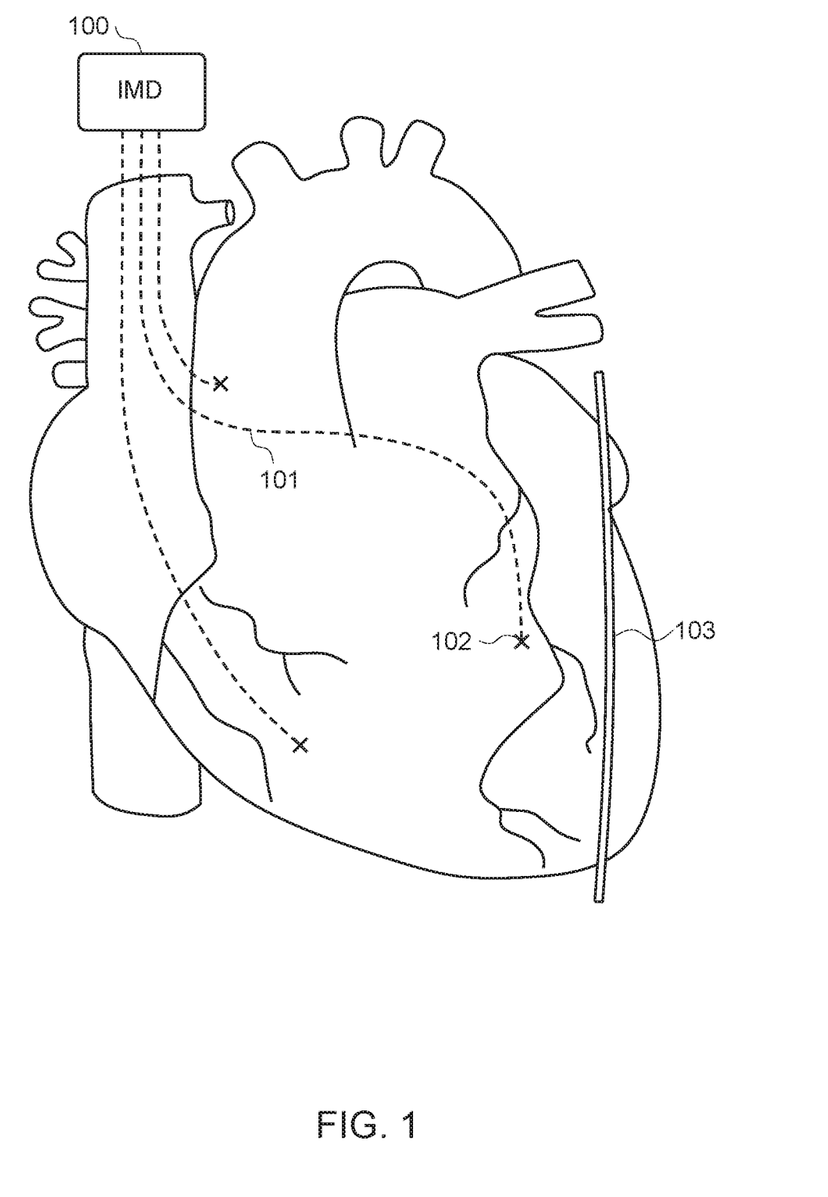
FIG. 1 illustrates, by way of example, an embodiment of an implantable medical device (IMD) configured to deliver myocardial stimulation.

FIG. 1 illustrates, by way of an example, an implantable medical device (IMD) 100 coupled to a patient's heart and configured to deliver myocardial stimulation for pacing therapy and/or sense cardiac events. The IMD 100 can be used to deliver a cardiac tissue stimulation therapy, such as a cardiac rhythm management therapy (CRT) or other pacing therapies, using leads represented by the dotted lines and electrodes represented by "X" fed into the right atrium, right ventricle, and coronary sinus of the heart. The lead 101 passing through the coronary sinus of the heart includes a left ventricular (LV) electrode 102, or electrodes, for use to stimulate the left ventricle at a stimulation site. In an example, the lead 101 can be a multipolar lead, including a plurality of electrodes and corresponding conductors. In an example, the lead 101 can include four discrete electrodes, such as: a tip electrode, a first ring electrode, a second ring electrode, and a third ring electrode. In an example, the electrodes can be located near a distal portion of the lead 101. Similarly the IMD 100 can include a lead positioned to stimulate the right ventricle (RV) and including a plurality of electrodes, such as a tip electrode and one or more ring electrodes. The IMD 100 can itself be configured as a Can electrode by using a conductive housing of the IMD 100. Electric potential developed between different electrodes can be used to provide a plurality of pacing configurations of pacing vectors available in the IMD 100. The pacing configurations involving LV electrodes use the LV electrode 102, which may be relatively close to a left phrenic nerve 103 of the patient. PS may occur for certain configurations of pacing vectors or electrode placement.

PS may also occur due to certain factors including but not limited to changes in the patient's body position, LV lead micro-dislodgement, cardiac reverse remodeling, changes in a stimulation threshold associated with PS, referred to herein as a PS threshold, or any other such factor. For example, PS can occur due to dislodgement of an acutely implanted lead or a chronically implanted lead. PS can occur more frequently in an acutely implanted lead as compared to a chronically implanted lead due to relative instability of the acutely-implanted lead. As the acutely implanted lead remains implanted for a larger period of time, tissue growth can occur around the lead. This imparts relative stability to the lead. Increased stability can then cause changes in the manner in which the lead affects PS. Thus, PS threshold can be unstable and vary with a number of factors. The instability of PS can be more frequent in an ambulatory setting rather than in a clinical setting. Detection of PS in the ambulatory setting can involve using a plurality of sensors. Various examples of the present subject matter can be used in processes for using PS sensor(s) to detect PS. A PS sensor can be used to detect phrenic nerve activity. By way of example and not limitation, a PS sensor can detect motion caused by the diaphragm induced by PS. For example, some examples can use an accelerometer to detect PS. Other examples of sensors that can be used to detect PS include, but are not limited to, a posture sensor, an acoustic sensor, a respiration sensor, an impedance sensor, a neural sensor on the phrenic nerve, a metabolic sensor, or an electromyogram (EMG) sensor for sensing signals indicative of diaphragm contraction. Some examples use a posture sensor to provide context. Some examples use an activity sensor to provide context. Some examples use a timer to determine a time of day to provide context. Some examples allow the device to store posture, activity, time of day and the like with the detected PS data to determine the context when the PS is observed.

Figure 2:
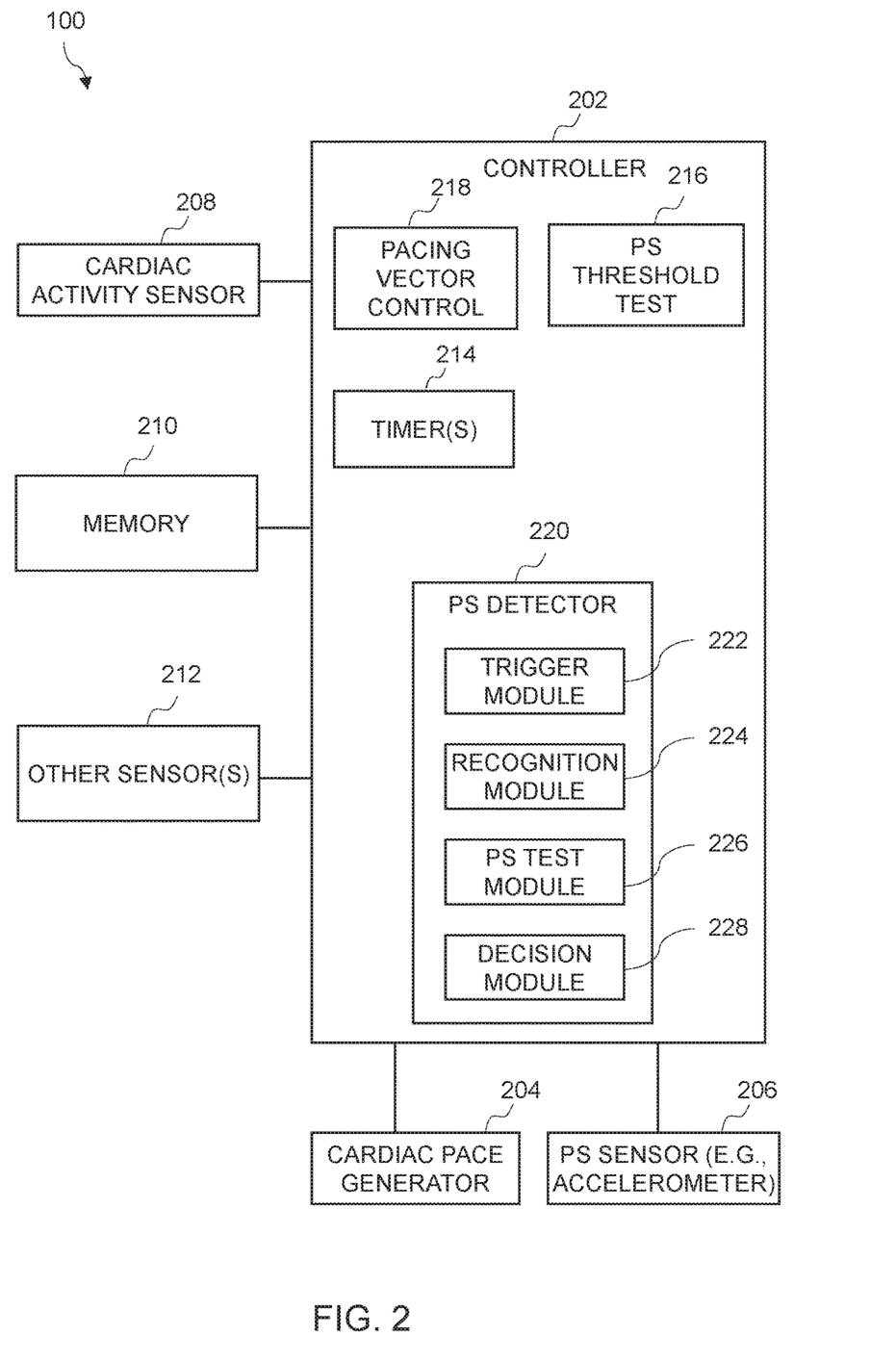
FIG. 2 illustrates, by way of example, an embodiment of an IMD.

FIG. 2 illustrates an example of the implantable medical device (IMD) 100. The IMD 100 includes a controller 202, a cardiac pace generator 206, a PS sensor 206, a cardiac activity sensor 208, a memory 210 and other sensor(s) 212. In various examples, the one or more other sensors 212 can include, by way of example and not limitation, a sensor used for detecting posture, a sensor used for detecting respiration or a respiration cycle, a metabolic sensor, a pressure sensor, a temperature sensor, a minute ventilation sensor, an impedance sensor, a muscle noise sensor, or a sensor used for detecting activity. The controller 202 can include one or more timer(s) 214, a PS threshold test module 216, a pacing vector control module 218, and an ambulatory PS detector 220. The ambulatory PS detector 220 may include a trigger module 222, a recognition module 224, a PS test module 226, and a decision module 228.

In an example, the IMD 100 can implement a cardiac pacing algorithm, in which the controller 202 receives sensed cardiac activity from the cardiac activity sensor 208, uses timer(s) 214, such as a cardiac pacing timer, to determine a pace time for delivering a cardiac pace or other myocardial stimulation pulse, and controls the cardiac pace generator 204 to deliver the cardiac pace at the desired time. The IMD 100 can store data associated with the cardiac pacing algorithm, as well as other data, such as data from other sensors 212 or data associated with the ambulatory PS detector 220 in the memory 210 of the IMD 100.

The PS threshold test module may be configured to determine PS thresholds for different available pacing configurations. The PS threshold represents a boundary for pacing parameters separating parameter(s) when PS may be observed and parameter(s) when PS is not expected to be observed. The pacing configurations may be controlled using the pacing vector control 218 module The controller 202 can include the PS detector 220 which can be configured to detect PS during myocardial stimulation. As it forms part of IMD 100, the ambulatory PS detector 220 can be used to detect PS in ambulatory patients. In some examples, the PS detector 220 includes the trigger module and the decision module. In some examples, the PS detector includes the trigger module, the recognition module and the decision module. In some examples, the ambulatory PS detector includes the trigger module 222, the recognition module 224, the PS test module 226 and the decision module 228.

The trigger module 222 can be configured to monitor one or more sensors to receive a trigger to conduct a PS procedure in response to the trigger. The sensor(s) include the PS sensor, such as an accelerometer. However, the sensor(s) may also include other sensor(s) 212. The trigger can be defined based on an output of the sensor(s). For example, the trigger module 222 can be configured to monitor the accelerometer of the PS sensor 206 to determine when a signal from the accelerometer crosses a predefined amplitude threshold that functions as a trigger threshold. In some example, a threshold may function as the trigger threshold. The crossing of the predefined amplitude threshold by the accelerometer signal during PS threshold test can then be defined as the trigger for conducting the PS procedure. However, the trigger threshold may be other trigger(s) to be more inclusive of signals that may potentially include PS. At least one other trigger can be defined including, but not limited to, a time duration expiration (such as trigger PS procedure every "X" hours, or "Y" days post implant), an LV Auto-Threshold (LVAT) test which automatically determines the threshold for capturing myocardia, a lead dislodgement event, a pacing parameter change, a detection of reverse remodeling, a user-initiation of the PS procedure, or feature(s) of the sensed signal other than or in addition to amplitude. In an example, a combination of triggers can be used as the trigger for conducting the PS procedure.

The trigger received by the trigger module 222 may be adequate to identify PS. However, some examples provide one or more additional module(s) (recognition module 224 and/or PS test module 226) to further analyze the sensed signal to ensure the accuracy of PS indication. That is, these additional module(s) may provide higher level(s) of confidence that PS has occurred.

For example, the recognition module 224 can be configured to analyze the signal to confirm the presence of PS. In a sense, the recognition module 224 may function as an intermediate PS test by analyzing more of the sensed signal than the trigger module 222, and may function as a "gate keeper" before a more robust PS test is conducted by a PS test module 226. In an example, the recognition module 224 can be configured to store information pertinent to the signal. For example, the recognition module 224 can be configured to respond to the trigger from the trigger module 222 and record the sensed signal for a certain amount of time. The stored signal may be a raw signal from the sensor or may be a filtered signal. In an example, the signal may be continually recorded in a circular buffer storage rather than only being recorded in response to the trigger from the trigger module 222. Thus, for example, if the trigger module 222 is configured to provide a trigger when an amplitude of the sensed signal crosses a threshold, the recognition module can evaluate the stored signal to confirm that the stored signal is consistent with PS. For example, the recognition module 224 may store T seconds of the sensed signal for further analysis.

In an example, the recognition module 224 can be configured to have at least some capabilities to change certain device sensing/pacing parameters. Some examples of active capabilities include but are not limited to forcing a maximum output pacing limited by a ceiling in the current pacing vector or forcing a minimum output pacing limited by a floor in the current vector. Some other examples of active capabilities include pacing in refractory of the heart, which ensures sensing of the PS response rather than a response to cardiac capture (such as heart sounds). Some embodiments may implement the recognition module in hardware, and some examples may implement the recognition module in firmware. The recognition module 224 may analyze PS beats to confirm that the evaluated signal is consistent with PS if M of N PS beats are confirmed as being consistent with PS. A PS beat is a PS signal associated with a cardiac pace. If the recognition module 224 confirms that the evaluated signal is consistent with PS, then some embodiments may initiate a more robust test using the PS test module 226. Some embodiments will instead trigger the decision module 228 if the recognition module 224 confirms that the evaluated signal is consistent with PS.

The PS test module may implement one or more of the PS detection algorithms disclosed in U.S. application Ser. No. 13/781,133 entitled "Baseline Determination For Phrenic Nerve Stimulation Detection" filed Feb. 28, 2013, U.S. application Ser. No. 13/781,042 entitled "Determination of Phrenic Nerve Stimulation Threshold" filed Feb. 28, 2013, and U.S. application Ser. No. 13/781,177 entitled "Phrenic Nerve Stimulation Detection" filed Feb. 28, 2013, and U.S.

App. No. 61/670,870 entitled "Adapted Phrenic Nerve Stimulation Detection." filed Jul. 12, 2012.

By way of example, a relatively simple PS test may be implemented to detect for PS presence only in the current pacing vector, a more moderate PS test may be implemented to detect for PS presence in a user-limited list of available pacing vectors, and a more complex PS test may be implemented to detect for PS presence in all available pacing vectors. A pacing vector represents some combination of source and sink electrodes. An example of a user-limited list of available pacing vectors is a list of vectors having a common or default anode/return electrode. Some embodiments may change the device settings to search for PS. The results of these tests may provide the decision module 228 with information for an ambulatory vector change and/be stored and presented at patient follow-up visits to simplify pacing reprogramming. The exhaustive threshold search in all vectors may work with an auto-threshold algorithm, such as LV auto-threshold (LVAT) algorithms, for example, to recall or to newly determine pacing thresholds, allowing the identification of the next best pacing vector.

An outcome of the PS test module 226 can be used to decide whether the current or any other pacing configuration causes the occurrence of the PS. Accordingly the IMD 100 can be reprogrammed to adjust or change one or more parameters that may be associated with the pacing configuration causing PS.

The decision module 228 can be configured to take action based on the outcome of the PS test module 226, or to take action based on the outcome of the recognition module 224, or to take action based on the outcome of the trigger module 222. In an example, the decision module 228 can be configured to store a PS presence indicator in the storage of the IMD 100, such as in the memory 210, based on the outcome of the PS test module 226. In an example, the decision module 228 can be configured to automatically switch the pacing configuration of the IMD 100 to avoid PS. In an example, the decision module 228 can be configured to send an alert to an external system after the detection of PS. In an example, the external system can be a programmer configured to communicate with the IMD 100. In an example, the external system can communicate with the IMD 100 over a telemetry link.

In an example, the user may desire automatic device adjustments to be made to avoid PS. In an example, a physician can physically move the electrode. Some examples can provide electronic repositioning by selecting a set of stimulation electrodes from a larger set of potential stimulation electrodes. In some embodiments, the pacing vector between or among stimulation electrodes can be modified in an attempt to avoid PS. The controller 202 in some IMD 100 embodiments can include the pacing vector control module 218 which can be used to change the pacing vectors. The pacing vector control can be implemented under the control of a clinician through an external programmer, or can be implemented autonomously by the IMD 100 such as in an ambulatory setting. The PS detection can occur in the same IMD 100 that is providing the myocardial stimulation, or can occur in another internal system. In an example, the other internal system can be another IMD.

Figure 3:
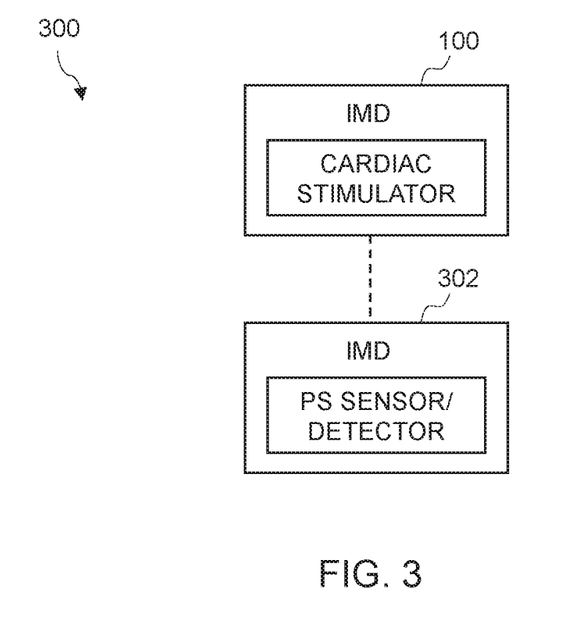
FIG. 3 illustrates, by way of example, an embodiment of a system that includes two or more IMDs.

FIG. 3 illustrates an example of a system 300 that includes two or more IMDs. A first one of the IMDs 100 in the illustrated system includes a cardiac stimulator configured to deliver myocardial stimulation pulses. By way of example and not limitation, the first IMD 100 can be a pacemaker or other cardiac rhythm management device. A second one of the IMDs 302 in the illustrated system includes a PS detector/sensor used to detect PS that can be caused by the myocardial stimulation pulses delivered from the first one of the IMDs. In an example, the PS detector/sensor can include an accelerometer that can be configured to detect the presence of PS during myocardial stimulation. The accelerometer can provide a signal to the controller 202 of the IMD 100 for use to detect PS. In some embodiments, the IMDs 100, 302 can communicate with each other over a wired connection. In some embodiments, the IMDs 100, 302 can communicate with each other wirelessly using ultrasound or radiofrequency (RF) or other wireless technology. The sensor(s) used for detecting PS can be implanted or can be external. The algorithms for processing the sensed signals to detect PS can be performed within the IMD(s) and/or can be performed in external devices. In an example PS can be detected using the one or more sensors that can be implantable within the patient, while the processing of the sensed signals can be performed by external device(s). The monitoring of the patient for PS can be performed in a clinical setting or in an ambulatory setting. This monitoring, regardless of whether it is performed in the clinical setting or an ambulatory setting, can be performed using implanted PS detectors such as illustrated in FIGS. 2-3, for example, and/or can be performed using external PS detectors.

Figure 4:
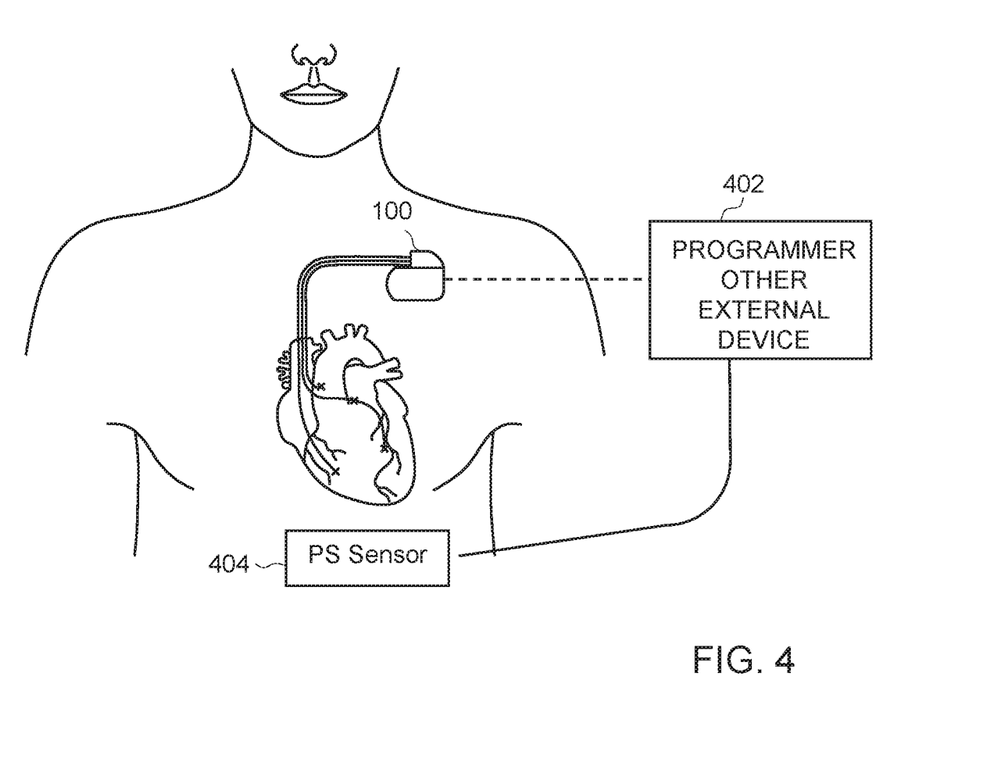
FIG. 4 illustrates, by way of example, an embodiment of a system that includes the IMD, such as a cardiac rhythm management device, an external device such as a programmer, and an external PS sensor.

FIG. 4 illustrates an embodiment of a system that includes the IMD 100, such as a cardiac rhythm management device, an external device 402 such as a programmer, and an external PS sensor 404. The system can be implemented in a clinical setting, such as by a clinician who uses a programmer to program the IMD 100, or can be implemented by the patient in an ambulatory setting to occasionally check if the myocardial stimulation is causing PS. In an example, the external device 402 includes a PS detector that cooperates with the PS sensor to discriminate if a signal from the PS sensor indicates PS. In an example, the PS detector can be configured as the PS detector 220 discussed in FIG. 2. In various embodiments, the external device includes a PS threshold test module used to perform PS threshold test(s). The PS threshold test can be configured to control the IMD 100 to deliver myocardial stimulation using different stimulation parameters. The PS threshold tests can be configured to determine the myocardial stimulation parameters that cause or that can cause PS, or myocardial stimulation parameters that do not cause PS. The physical position of the stimulation electrode or electrodes used to deliver the myocardial stimulation can be adjusted in an attempt to avoid PS, such as can occur during an implantation procedure. In some examples, the pacing vector between or among stimulation electrodes can be modified in an attempt to avoid PS. In some examples, the external PS sensor 404 can be integrated with the external device 402, such that the PS can be sensed by holding or otherwise positioning the external device next to the patient (e.g. externally positioned near the diaphragm or near the apex of the heart) to allow the PS sensor (e.g. an accelerometer in the device) to sense PS.

The external PS sensor 404 can include a two-axis or a three-axis accelerometer for sensing PS in a pacing configuration of the IMD 100. As previously discussed, pacing pulses delivered by the IMD 100 can stimulate the phrenic nerve and cause contraction of the diaphragm resulting in PS presence. Abrupt contractions of the diaphragm can be sensed by the accelerometer. The signal from the accelerometer can be used to detect PS which can be stored in the memory of the IMD along with the pacing configuration data. In some examples, PS detection and corresponding PS data storing can be performed for all available pacing configurations or a subset of all available pacing configurations in the IMD 100.

Figure 5:
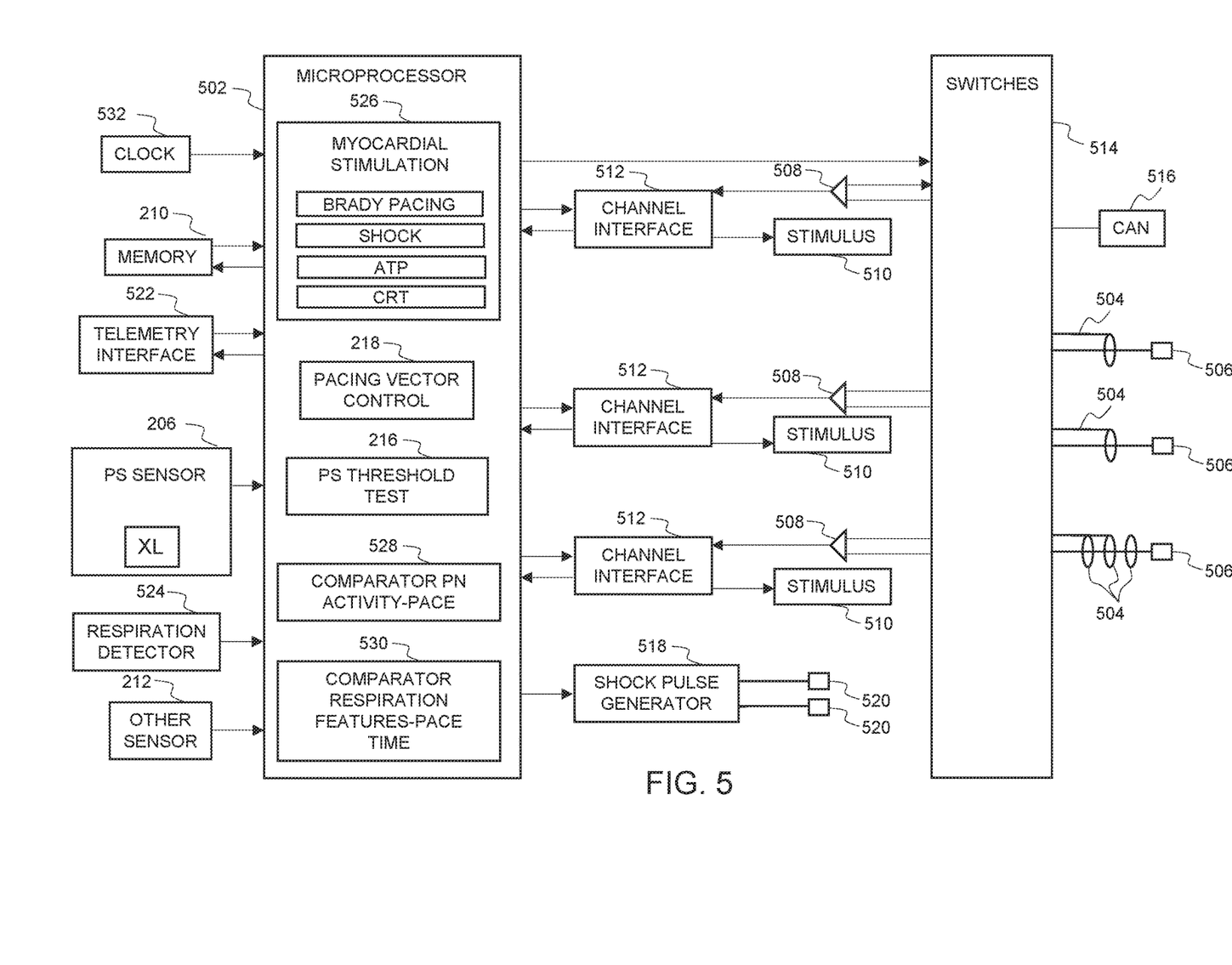
FIG. 5 illustrates, by way of example, a system diagram of an embodiment of a microprocessor-based implantable device.

FIG. 5 illustrates a system diagram of an example of a microprocessor based implantable device. The controller of the device is a microprocessor 502 which communicates with a memory 210 via a bidirectional data bus. The controller can be implemented by other types of logic circuitry (e.g., discrete components or programmable logic arrays) using a state machine type of design. As used herein, the term "circuitry" should be taken to refer to either discrete logic circuitry, firmware, or to the programming of a microprocessor. Shown in the figure are three examples of sensing and pacing channels. Each channel may include a lead with a ring electrode 504 and a tip electrode, a sensing amplifier 508, a pulse generator 510, and a channel interface 512. One of the illustrated leads includes multiple ring electrodes 504, such as can be used in a multi-polar lead. An example of a multipolar lead is a left ventricle quadripolar lead. In some examples, the leads of the cardiac stimulation electrodes are replaced by wireless links. Each channel thus includes a pacing channel made up of the pulse generator connected to the electrode and a sensing channel made up of the sense amplifier connected to the electrode. The channel interfaces communicate bidirectionally with the microprocessor 502, and each interface can include analog-to-digital converters for digitizing sensing signal inputs from the sensing amplifiers and registers that can be written to by the microprocessor 502 in order to output pacing pulses, change the pacing pulse amplitude, and adjust the gain and threshold values for the sensing amplifiers 508. The sensing circuitry of the pacemaker detects intrinsic chamber activity, termed either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias. The electrodes of each lead are connected via conductors within the lead to a switching network 514 controlled by the microprocessor. The switching network 514 is used to switch the electrodes to the input of a sense amplifier in order to detect intrinsic cardiac activity and to the output of a pulse generator in order to deliver a pacing pulse. The switching network 514 also enables the device to sense or pace either in a bipolar mode using both the ring and tip electrodes of a lead or in unipolar or an extended bipolar mode using only one of the electrodes of the lead with the device housing (can) 516 or an electrode on another lead serving as the return electrode. In some examples, a shock pulse generator 518 can be interfaced to the controller, in addition or alternative to other stimulation channels, for delivering a defibrillation shock via a pair of shock electrodes 520 to the atria or ventricles upon detection of a shockable tachyarrhythmia. A can electrode can also be used to deliver shocks. The figure illustrates a telemetry interface 522 connected to the microprocessor 502, which can be used to communicate with an external device. As illustrated in FIG. 5, the system can include a PS sensor 206. According to various examples, the phrenic nerve activity detector can include, but is not limited to, an accelerometer, an acoustic sensor, a respiration sensor, impedance sensors, neural sensor on the phrenic nerve, or electrodes to sense electromyogram signals indicative of diaphragm contraction. Various examples use more than one detector to provide a composite signal that indicates phrenic nerve capture. The use of more than one detector can enhance the confidence in detecting PS. The illustrated example also includes a clock 532.

According to various examples, the illustrated microprocessor 502 can be configured to perform various cardiac tissue (e.g. myocardial) stimulation routines 526. Examples of myocardial therapy routines include bradycardia pacing therapies, antitachycardia shock therapies such as cardioversion or defibrillation therapies, antitachycardia pacing therapies (ATP), and cardiac resynchronization therapies (CRT). As illustrated, the controller 502 can also include a comparator 528 to compare time when phrenic nerve activity is detected to a pace time to determine that phrenic nerve activity is attributed to the pace, and/or can includes a comparator 530 to compare respiration features to the pace time for use in detecting PS. The illustrated microprocessor 502 can include instructions for performing a PS threshold test 216 and a pacing vector control process 218, similar to the controller 502 illustrated in FIG. 2. In an example, the PS threshold test 216 can be performed to confirm the PS presence and can be performed by the recognition module 224 of the controller 502 as discussed in conjunction with FIG. 2.

The microprocessor 502 can control the overall operation of the IMD 100 in accordance with programmed instructions stored in the memory 210. In an example, the microprocessor 502 can be configured to perform the phrenic stimulation (PS) detection procedure. In an example where the PS sensor 206 includes an accelerometer, the PS detection procedure can include performing a base test by sensing the amplitude of the accelerometer signal. The microprocessor 502 can further be configured to compare the sensed amplitude of the signal to a threshold amplitude value. The PS data derived from the comparison can then be stored in the memory 210 of the IMD 100. For example, the microprocessor 502 can perform the base test for a current pacing configuration of the IMD 100 implanted within a patient to detect the presence of PS and store the results of the test. When the patient visits a physician during a regular check-up routine, the physician can check the data stored in the memory to check the suitability or performance of the IMD 100 in the current pacing configuration. If the physician identifies that current pacing configuration is causing PS, the physician can change the parameters of the current pacing configuration. The physician can also switch the IMD 100 to another pacing configuration. In an example, the physician can check the PS data for all the available pacing configurations in the IMD 100. The PS data may be acquired during a visit to the clinic, or when the patient is ambulatory away from the clinic. In an example, the PS data for all the pacing configurations can be checked in accordance with the functioning of the PS test module 226 of the ambulatory PS detector 220 as discussed previously in FIG. 2. The PS data obtained from the PS test can be stored in the IMD 100 by performing the PS procedure for all the available pacing configurations in the IMD 100, and can be used as required.

Figure 6A:
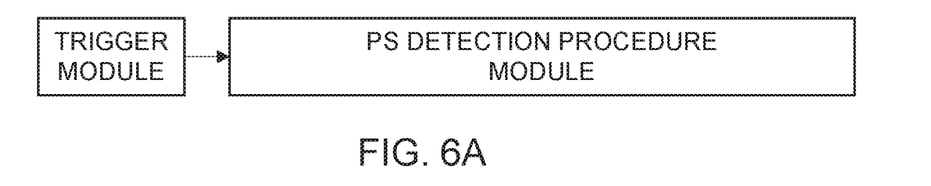
FIGS. 6A-6E illustrate, by way of example, various embodiments of a system for performing a PS detection procedure.
Figure 6B:
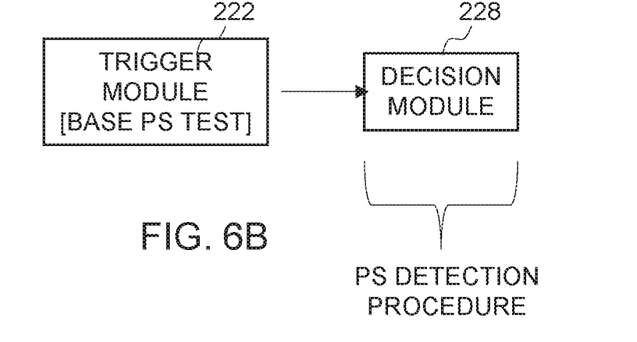
Figure 6C:
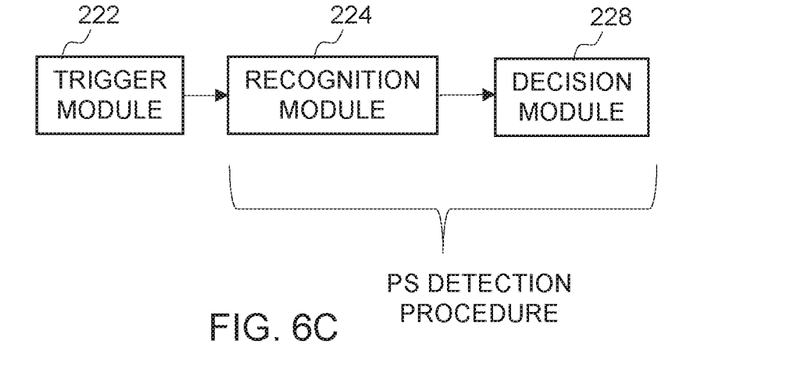
Figure 6D:
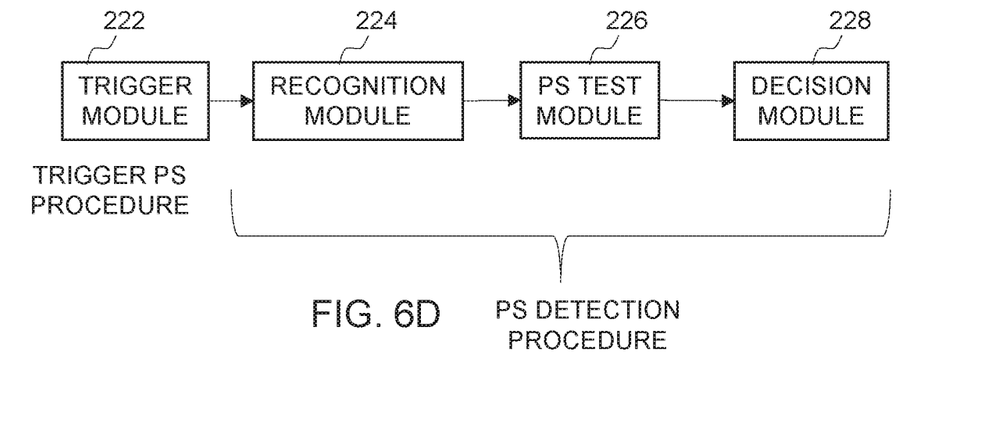

FIGS. 6A-6E illustrate, by way of example, various embodiments of a system 600 for performing a PS detection procedure, such as may be implemented using a PS detector similar to PS detector 220 illustrated in FIG. 2. FIG. 6A illustrates a procedure in which a trigger module triggers a PS detection module. The PS detection module may include the decision module 228 as illustrated in FIG. 6B, may include the recognition module 224 and decision module 228 as illustrated in FIG. 6C, or may include the recognition module 224, PS test module 226 and decision module 228 as illustrated in FIG. 6D. These modules have been previously discussed with respect to FIG. 2. Some embodiments may include the trigger module 222, the recognition module 224 and the decision module 228. Some embodiments may include the trigger module 222, the PS test module 226, and the decision module 228. A base test to detect PS may be performed, such as by trigger module 222, and another test may be performed to confirm the PS, such as by the recognition module or the PS test module, and a decision can be made based on the test results. In addition to performing the other test to confirm the PS, some embodiments may perform yet another PS detection test to further confirm the PS with greater confidence.

Figure 6E:
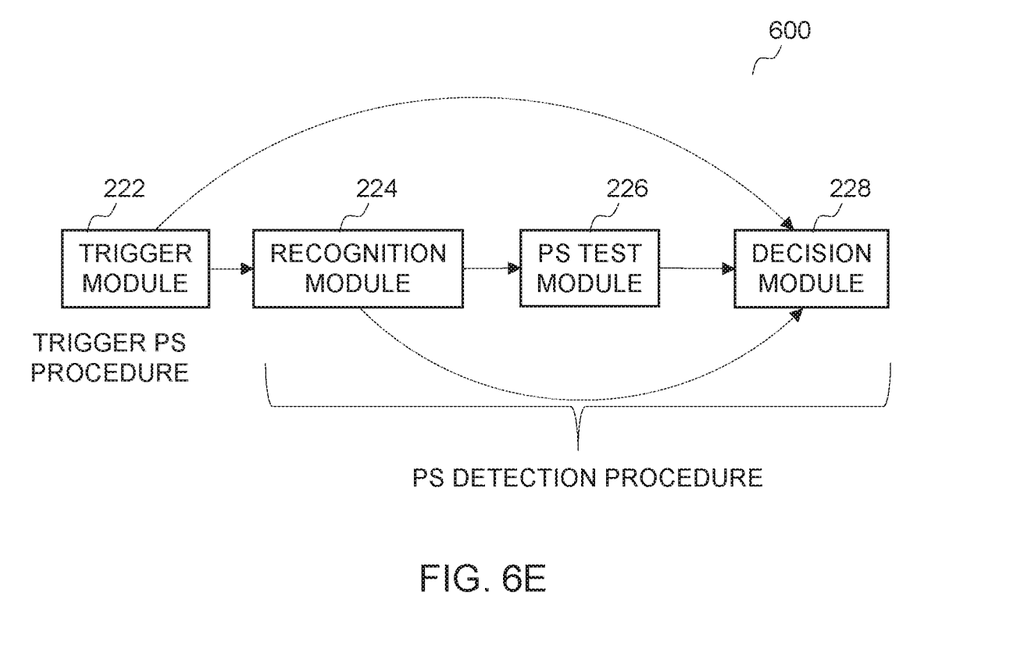

FIG. 6E illustrates an example in which the PS detection module includes the recognition module 224, PS test module 226 and decision module 228, and also includes programmable instructions for controlling which modules are implemented in the PS detection module. For example, the top arrow from the trigger module 222 to the decision module 228 illustrates that that recognition module 224 and PS test module 226 can be bypassed, and the bottom arrow from the recognition module 224 to the decision module 228 indicates that the PS test module 226 can be bypassed.

Figure 7:
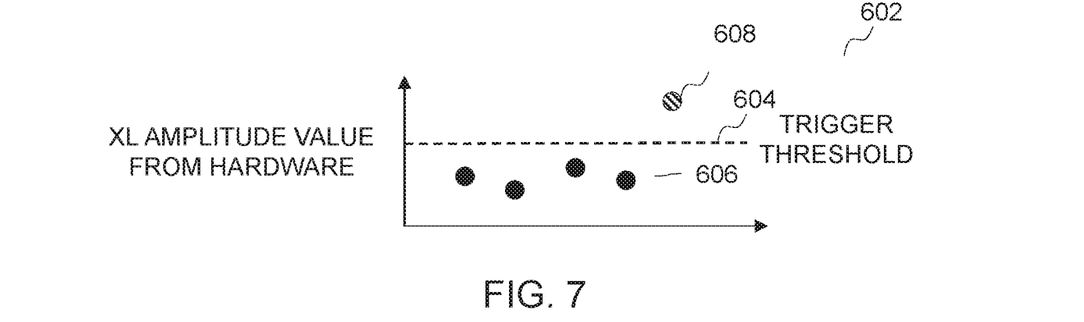
FIG. 7 illustrates an example of using a threshold 604 for an amplitude of signal from a PS sensor to trigger a PS detection routine.

FIG. 7 illustrates an example of using a threshold 604 for an amplitude of signal from a PS sensor to trigger a PS detection routine. For example, the trigger module 222 illustrated in FIGS. 6A-6E may implement the example. Amplitude values 606, 608 of the sensor signal (e.g. accelerometer signal) may be compared against the trigger threshold 604. Data collection is not continuous. The sensor signal may be sampled, and the sampling of the sensor signal may be at a low sampling frequency. If the amplitude value 606 is less than the trigger threshold 604, the trigger module 222 does not trigger the PS detection routine but rather continues to monitor the PS sensor signal. If the amplitude value 608 is greater than the trigger threshold 604, then the trigger module 222 may trigger the PS detection routine.

Figure 8A:
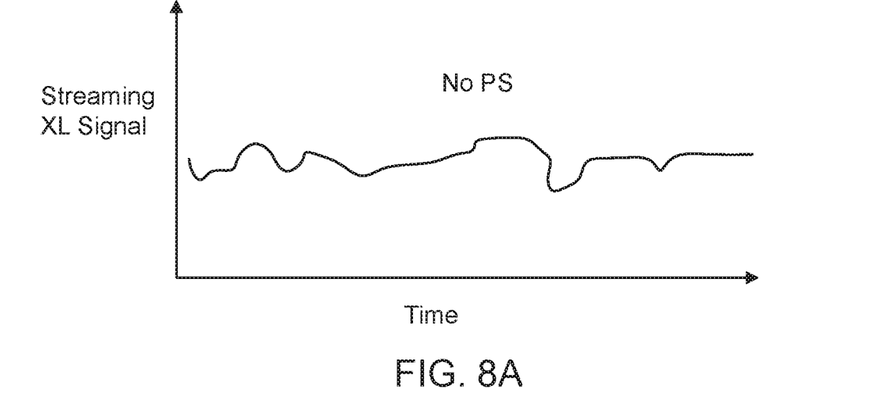
FIGS. 8A-8B illustrate an example of streaming signal from an accelerometer XL, where
Figure 8B:
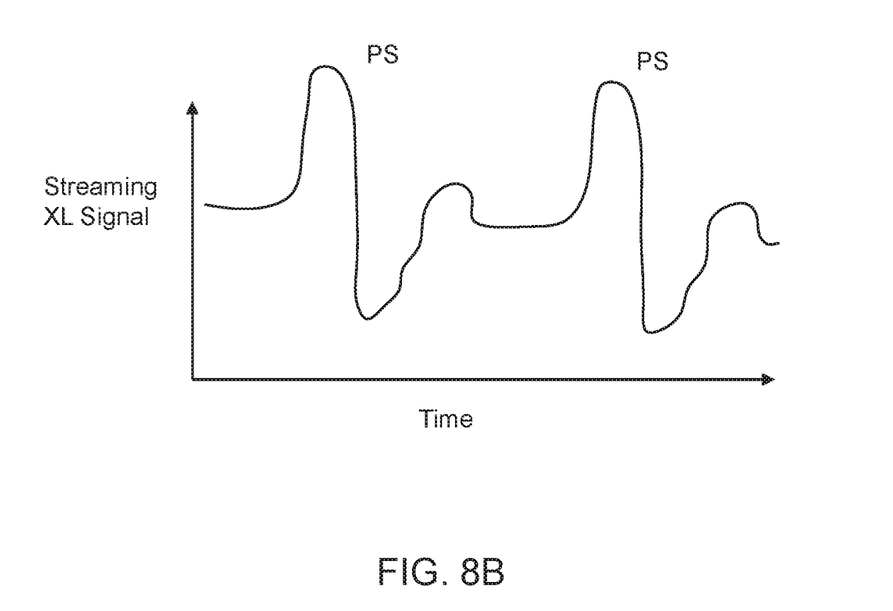

The PS sensor signal may be collected continuously, such as by streaming the signal. FIGS. 8A-8B illustrate an example of streaming signal from an accelerometer XL, where FIG. 8A illustrates no PS in the streaming signal and FIG. 8B illustrates occurrences of PS in the streaming signal. The recognition module 224 may evaluate a portion of the streaming signal, in response to a trigger from the trigger module, to detect PS.

Analysis of the signal by the recognition module 224 can prevent false positive triggers from activating further PS presence search across pacing configurations, which can be a power intensive process. If the analysis of the signal by the recognition module 224 confirms the presence of PS, any of the full-test module 226 or the decision module 228 can be activated.

In an example, the confirmation of the PS presence by the recognition module 224 can activate the PS test module 226. The PS test module 226 can be configured to analyze the signal from the accelerometer XL for each of a plurality of potential pacing configurations from the two or more pacing configurations that can be programmed in the IMD 100. The plurality of potential pacing configurations can each have a different cathode for delivering myocardial stimulation. More than one potential pacing configuration may have a common cathode. The PS test module 226 can be configured to analyze the signal from the accelerometer XL for each cathode used in the potential pacing configurations. In an example, IMD 100 can be programmed for the plurality of pacing configurations. In an example, the PS test module 226 can be configured to determine left ventricular thresholds for detecting PS in each of the plurality of potential pacing configurations. In an example, the PS test module 226 can be configured to perform a test that can be programmed by a user of the IMD 100, such as either the physician or the patient, to analyze and confirm PS for each of the plurality of potential pacing configurations using the PS test. In an example, the confirmation of PS presence by the recognition module 224 can activate the decision module 228. The decision module 228 can then be configured to take any of the actions discussed previously to cause storing, reporting or mitigation of the PS.

Figure 9A:
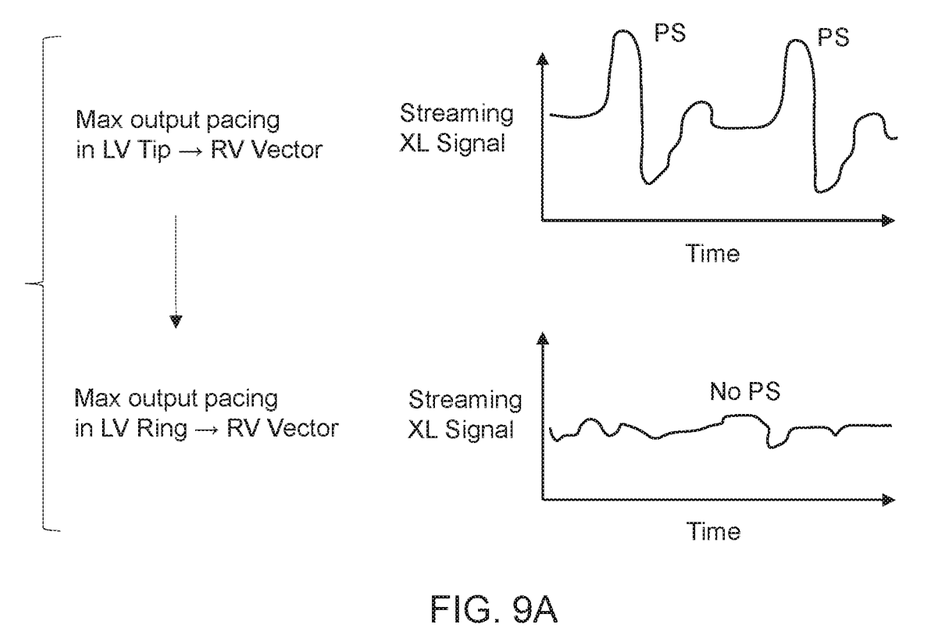
FIGS. 9A-9B illustrate schematic diagrams for an example of performing a PS test across two potential pacing configurations and storing the results of the test.
Figure 9B:
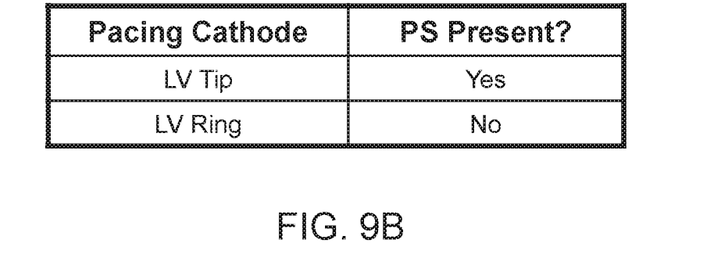

FIGS. 9A-9B illustrate schematic diagrams for an example of performing a PS test across two potential pacing configurations and storing the results of the test. Some examples include but are not limited to forcing a maximum output pacing limited by a ceiling in a current pacing vector or forcing a minimum output pacing limited by a floor in the current vector. Some examples include a step-wise voltage/pulse width test. FIG. 9A illustrate a streaming PS sensor signal, and further indicate a signal in which PS is found (top) and a signal in which PS is not found (bottom). Thus, the decision module 228 may record the PS results (e.g. FIG. 9B) and may change the pacing configuration from LV Tip→RV Vector to LV Ring→RV Vector to avoid PS.

As will be understood by those of ordinary skill in the art, at least part of the processes may be implemented using a machine or computer using instructions encoded on a machine-readable or computer-readable medium. It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system, comprising:
an implantable medical device (IMD) configured for implantation in a patient and configured for delivering pacing energy to the patient using a pacing configuration for a prescribed myocardial therapy to provide a therapeutic benefit to the patient in an ambulatory setting, the IMD including a cardiac pace generator, a cardiac activity sensor, a memory, a controller and at least one phrenic nerve stimulation (PS) sensor, wherein the controller is configured to:
cooperate with the cardiac pace generator and the cardiac activity sensor to control timing for delivering the pacing energy;
monitor at least one PS sensor when providing the prescribed myocardial therapy using the pacing configuration to generate a monitored sensor signal;
determine a PS event, which indicates that phrenic nerve stimulation was observed when delivering the pacing energy using the pacing configuration, using the monitored sensor signal, wherein the PS event is determined by detecting a first potential PS event and triggering a response to the detected first potential PS event to confirm the PS event with a higher level of confidence than if only the first potential PS event was used,
wherein the first potential PS event is detected by sensing a first amplitude in the monitored signal and comparing the sensed first amplitude to a threshold, and
wherein the triggered response to the detected first potential PS event includes storing a portion of the monitored sensor signal and then analyzing more of the monitored signal other than the first amplitude using the stored portion of the monitored sensor signal to detect additional potential PS events in the stored portion of the monitored sensor signal to confirm the PS event;

determine contextual data for the PS event to provide context when the phrenic nerve stimulation was observed, wherein the contextual data is determined by determining a posture or an activity during a time when the phrenic nerve stimulation was observed or determining a time of day when the phrenic nerve stimulation was observed; and store the PS event indicating that the phrenic nerve stimulation was observed and the contextual data corresponding to the PS event in the memory of the IMD, wherein the stored contextual data provides context when the phrenic nerve stimulation was observed.

2. The system of claim 1, further comprising a contextual sensor configured for use in providing the contextual data corresponding to the PS event.

3. The system of claim 2, wherein the contextual sensor includes a posture sensor configured for use in providing posture data corresponding to the PS event to provide context regarding the posture, wherein the contextual data corresponding to the PS event includes the posture data.

4. The system of claim 2, wherein the contextual sensor includes an activity sensor configured for use in providing activity data corresponding to the PS event to provide the context regarding the activity, wherein the contextual data corresponding to the PS event includes the activity data.

5. The system of claim 1, further comprising a timer configured for use in providing a time of day corresponding to the PS event to provide context regarding the time of day, wherein the contextual data corresponding to the PS event includes the time of day.

6. The system of claim 1, wherein the at least one PS sensor includes an acoustic sensor or an accelerometer.

7. The system of claim 1, wherein the at least one PS sensor includes a respiration sensor.

8. The system of claim 1, wherein the at least one PS sensor includes an impedance sensor.

9. The system of claim 1, wherein the at least one PS sensor includes an electromyogram sensor.

10. The system of claim 1, wherein the at least one PS sensor includes a neural sensor for the phrenic nerve.

11. The system of claim 1, wherein the at least one PS sensor includes a metabolic sensor.

12. The system of claim 1, wherein the IMD is configured to use a pacing configuration to pace myocardia for the prescribed myocardial therapy, and the controller is configured to confirm the PS event by using the pacing configuration to deliver a pace during a refractory period of the heart and determining whether the at least one PS sensor indicates PS from the pace during the refractory period of the heart.

13. A method implemented using an implantable medical device (IMD) configured for implantation in a patient and configured for delivering pacing energy to the patient using a pacing configuration for a prescribed myocardial therapy to provide a therapeutic benefit to the patient in an ambulatory setting, the IMD including a cardiac pace generator, a cardiac activity sensor, a memory, a controller and at least one phrenic nerve stimulation (PS) sensor, wherein the method includes using the controller to:

control timing for delivering the pacing energy;

monitor at least one PS sensor when providing the prescribed myocardial therapy using the pacing configuration to generate a monitored sensor signal, determine a PS event, which indicates that phrenic nerve stimulation was observed when delivering the pacing energy using the pacing configuration, using the monitored sensor signal, wherein the PS event is determined by detecting a first potential PS event and triggering a response to the detected first potential PS event to confirm the PS event with a higher level of confidence than if only the first potential PS event was used, wherein the first potential PS event is detected by sensing a first amplitude in the monitored sensor signal and comparing the sensed first amplitude to a threshold, and wherein the triggered response to the detected first potential PS event includes storing a portion of the monitored senor signal and then analyzing more of the monitored signal other than the first amplitude using the stored portion of the monitored sensor signal to detect additional potential PS events in the stored portion of the monitored sensor signal to confirm the PS event;

determine contextual data for the PS event to provide context when the phrenic nerve stimulation was observed, wherein the contextual data is determined by determining a posture or an activity during a time when the phrenic nerve stimulation was observed or determining a time of day when the phrenic nerve stimulation was observed; and store the PS event indicating that the phrenic nerve stimulation was observed and the contextual data for the PS event in the memory of the IMD, wherein the stored contextual data provides context when the phrenic nerve stimulation was observed.

14. The method of claim 13, wherein using the controller to determine contextual data corresponding to the PS event includes using a posture sensor to determine the contextual data corresponding to the PS event to provide context regarding the posture.

15. The method of claim 13, wherein using the controller to determine contextual data corresponding to the PS event includes using an activity sensor to determine the contextual data corresponding to the PS event to provide context regarding the activity.

16. The method of claim 13, wherein using the controller to determine contextual data corresponding to the PS event includes using a timer configured for use in providing the time of day corresponding to the PS event, wherein the contextual data corresponding to the PS event includes the time of day.

17. A non-transitory machine-readable medium including instructions, which when executed by an implantable medical device (IMD) that is configured for implantation in a patient and configured for delivering pacing energy to the patient using a pacing configuration for the prescribed myocardial therapy to provide a therapeutic benefit to the patient in an ambulatory setting, cause the IMD to:

control timing for delivering pacing energy for the prescribed myocardial therapy;

monitor at least one PS sensor when providing the prescribed myocardial therapy using the pacing configuration to generate a monitored sensor signal, determine a PS event, which indicates that phrenic nerve stimulation was observed when delivering the pacing energy using the pacing configuration, using the monitored sensor signal, wherein the PS event is determined by detecting a first potential PS event and triggering a response to the detected first potential PS event to confirm the PS event with a higher level of confidence than if only the first potential PS event was used, wherein the first potential PS event is detected by sensing a first amplitude in the monitored sensor signal and comparing the sensed first amplitude to a threshold, and wherein the triggered response to the detected first potential PS event includes storing a portion of the monitored sensor signal and then analyzing more of the monitored signal other than the first amplitude using the stored portion of the monitored sensor signal to detect additional potential PS events in the stored portion of the monitored sensor signal to confirm the PS event;

determine contextual data for the PS event to provide context when the phrenic nerve stimulation was observed, wherein the contextual data is determined by determining a posture or an activity during a time when the phrenic nerve stimulation was observed or determining a time of day when the phrenic nerve stimulation was observed; and store the PS event indicating that the phrenic nerve stimulation was observed and the contextual data for the PS event in memory of the IMD, wherein the stored contextual data provides context when the phrenic nerve stimulation was observed.

18. The non-transitory machine-readable medium of claim 17, wherein the contextual data corresponding to the PS event includes posture data from a posture sensor to provide context regarding the posture.

19. The non-transitory machine-readable medium of claim 17, wherein the contextual data corresponding to the PS event includes activity data from an activity sensor to provide context regarding the activity.

20. The non-transitory machine-readable medium of claim 17, wherein the contextual data corresponding to the PS event includes the time of day.

* * * * *